United States Patent

Horne et al.

[11] Patent Number: 5,998,542
[45] Date of Patent: Dec. 7, 1999

[54] PROCESSING OF AN ELASTOMER DISPERSION

[75] Inventors: Adam J. Horne, Clifton Park; Donald S. Johnson, Scotia; John A. Kilgour, Clifton Park; Richard D. Wang, Rexford, all of N.Y.

[73] Assignee: General Electric Company, Waterford, N.Y.

[21] Appl. No.: 08/990,128

[22] Filed: Dec. 12, 1997

[51] Int. Cl.$^6$ ....................................................... C08J 5/54
[52] U.S. Cl. ........................ 524/731; 524/923; 524/924; 528/15; 528/31; 424/401; 523/223; 523/318
[58] Field of Search ................................ 524/731, 923, 524/924; 528/502, 15, 31; 424/401; 523/223, 318

[56] References Cited

U.S. PATENT DOCUMENTS

| | | |
|---|---|---|
| 4,780,145 | 10/1988 | Mori et al. . |
| 4,970,252 | 11/1990 | Sakuta et al. . |
| 4,983,388 | 1/1991 | Kuwata et al. . |
| 4,987,169 | 1/1991 | Kuwata et al. . |
| 5,236,986 | 8/1993 | Sakuta . |
| 5,403,580 | 4/1995 | Bujanowski et al. . |
| 5,468,477 | 11/1995 | Kumar et al. . |
| 5,760,116 | 6/1998 | Kilgour et al. ........................ 524/268 |
| 5,854,336 | 12/1998 | Divone, Sr. et al. . |

FOREIGN PATENT DOCUMENTS

WO 97/44010  11/1997  WIPO .

*Primary Examiner*—Robert Dawson
*Assistant Examiner*—Caixia Lu-Rutt
*Attorney, Agent, or Firm*—Kenneth S. Wheelock

[57] ABSTRACT

A composition comprising the hydrosilylation addition product of a linear alkenyl functionalized polyorganosiloxane and an $M^HQ$ resin and a low molecular weight silicone when subjected to a new particle size reduction process that includes flow induced shearing provides for components in personal care formulations that have improved spreadability and substance as a consequence of a unique particle size distribution.

12 Claims, No Drawings

PROCESSING OF AN ELASTOMER DISPERSION

FIELD OF THE INVENTION

The present invention relates to a silicone composition useful as a thickening agent for low molecular weight volatile silicones. The present invention also relates to a process for rendering silicone comprising gels flowable by the mixing low molecular weight silicones with the gel and processing the mixture.

BACKGROUND OF THE INVENTION

Silicones have many uses in a variety of fields. They have found large commercial application in products as diverse as sealants, silicone rubbers, adhesives and cosmetics. Silicone oils have been found to be particularly desirable components of cosmetic compositions because the materials impart a dry, smooth uniform feel to the cosmetic composition among other benefits such as increasing apparent luster (or shine). The general use of silicones in cosmetic formulations has been complicated somewhat by the facts that while lower molecular weight silicones impart desirable properties to a composition they are volatile and have low viscosity, while the silicones that overcome these disadvantages are undesirably viscous.

Thus when it has been desirable to utilize low viscosity silicone oils in a cosmetic application, thickening agents have been employed to increase the solution viscosity and slow down the evaporative loss of the volatile low molecular weight silicone oil. This procedure while effective has the disadvantage of decreasing the spreadability of the silicone oil and leaves a heavy greasy feel on the skin. The spreadability and dry smooth feel are properties associated with low viscosity silicone that imparts a desirable feel or hand to the composition when it is applied as a cosmetic formulation. Materials that have found application in attempting to retain the desirable properties of low molecular weight silicone oils in cosmetic compositions while reducing evaporative losses due to high volatility have been among others fatty acid esters of dextrin, fatty acid esters of sucrose, trimethylsilyl substituted polyvinyl alcohols, trimethylsilyl substituted poly saccharides, cellulose ethers containing fatty acid esters, and organically modified clay minerals. These materials have the disadvantage that the light feeling and spreadability imparted by the low viscosity silicone oil is changed with the result that the composition no longer possesses those properties that suggested the use of the low viscosity silicone oil in the first place. Another disadvantage of these thickening agents or volatility inhibitors is that a large number of them are water soluble and must be used as a water dispersions or solutions. With hydrophobic silicone oils the introduction of water thus necessitates the use of emulsifiers and compatibilizers, complicating the formulation of the cosmetic and generally lowering the stability of the formulation with respect to separation of the component phases.

Recently, another approach to retaining the properties of low viscosity silicone oils in cosmetic compositions has been advanced where the low viscosity silicone oil is combined with the addition polymerization product between an organohydrogen polysiloxane and an alkenyl functionalized organopolysiloxane (U.S. Pat. No. 4,987,169). The organolydrogen polysiloxane utilized in those formulations comprised $HSiO_{1.5}$ ($T^H$), $RSiO_{1.5}$ (T), $RHSiO$ ($D^H$), $R_2SiO$ (D), $R_2HSiO_{0.5}$ ($M^H$) and $R_3SiO_{0.5}$ (M) groups. The crosslinking hydride compound utilized was thus a compound of the general formula: $M_a M^H_b D_c D^H_d T_e T^H_f$. While the cross-linking compound admits T groups either as hydride or substituted by R the preference in this technology is for linear hydride materials because the addition polymerization proceeds more smoothly. The R groups in the above formulas are typical organic substituents known in the art. Subsequently a low molecular weight silicone oil is added to the cross-linked addition polymerized product and the mixture is treated by applying a shearing force. This material may be used by itself as a cosmetic component or as a thickening agent and has the properties of a grease and can be used in a wide variety of industrial lubrication applications as well as the cosmetic application contemplated. The material prepared in this manner can be regarded as a lightly cross-linked elastomer with a volatile, low molecular weight silicone oil dissolved therein. Because the precursor cross-linking hydride is preferably linear and only moderately branched when T groups are incorporated, the addition polymerized product does not possess a tight network of cross-links in the resulting polymer. Linear and lightly crosslinked networks suffer from the disadvantage of having lower efficiency in raising the viscosity of a low molecular weight silicone. In addition to increasing the cost of the product, higher levels of crosslinked silicones result in leaving behind more residue when the volatile, low molecular weight silicone evaporates during use. In some cosmetic applications, e.g. deodorant or antiperspirants, an increased residue is a significant disadvantage as it contributes to staining of the clothing.

Further, linear and lightly crosslinked silicones do not form a film as easily as more tightly crosslinked silicones. The lack of a formation of a film is a disadvantage in a cosmetic application because a film provides a softer, smoother feel as compared to the heavier, less desirable feel of a linear silicone.

For solids, size reduction processes generally result in changing both the average particle size and the particle size distribution. With most solid materials, size reduction techniques usually reduce the average article size and produce a Gaussian distribution of particle sizes. Consequently, the art dealing with size reduction techniques is primarily concerned with controlling the width of the Gaussian distribution, i.e. how broad or how narrow the particle size distribution is, a property typically measured by the width of the distribution peak at half the peak height of the most prevalent particle size. This is typically referred to as a half-width measurement.

Emulsions can also be subjected to size reduction processes with results similar to those obtained for solid processes. An initial particle size and particle size distribution of an immiscible liquid dispersed in a second liquid phase is converted to one having a smaller average particle size. Typically the particle size distribution of the discontinuous phase in an emulsion is best represented by a Gaussian distribution regardless of whether the particle size distribution is measured before or after size reduction.

In contrast to the somewhat well-known predictability of size reduction processes for solids and dispersed liquids, soft solids such as a polymer do not respond in a classical fashion. Unlike emulsions which are insensitive to different methods of applying a shear force to reduce the average particle size, soft polymers frequently yield a random manifold of sizes and shapes. Thus, where it is desirable to reduce the average particle size of an elastomer, it would represent an advance in the art if the result of the size reduction process was controllable, if not predictable.

SUMMARY OF THE INVENTION

We now disclose that tightly cross-linked elastomers prepared from the addition polymerization of an alkenyl organopolysiloxane and an $M^HQ$ resin may be combined with a volatile low molecular weight silicone oil and processed by flow induced shear to provide a desirable component for cosmetic compositions that possesses a unique particle size distribution.

The present invention thus provides for a process comprising:

a) subjecting a dispersion of an elastomer in a solvent to a pressure said elastomer having an initial average particle size and a particle size distribution;

b) subjecting said dispersion to a pressure drop through an orifice whereby said dispersion passes through said orifice wherein the initial average particle size of said dispersion is reduced; and c) repeating steps a) and b) whereby said particle size distribution is controlled and said particle size distribution comprises:
1) a local maximum ranging from about 21 to about 26 microns;
2) a local maximum ranging from about 33 to about 38 microns, and
3) a local maximum ranging from about 50 to 60 microns.

The present invention also provides for a process comprising:

a) subjecting a dispersion of an elastomer in a solvent to a pressure drop using an orifice said elastomer having an initial average particle size and a particle size distribution whereby said dispersion passes through said orifice wherein the initial average particle size of said dispersion is reduced; and b) repeating step a) whereby said particle size distribution is controlled and said particle size distribution comprises:
1) a local maximum ranging from about 21 to about 26 microns;
2) a local maximum ranging from about 33 to about 38 microns, and
3) a local maximum ranging from about 50 to 60 microns.

DETAILED DESCRIPTION OF THE INVENTION

The composition of a specific embodiment of the present invention comprises the hydrosilylation addition product of (1) a linear alkenyl stopped polyorganosiloxane having the formula:

$$M^{vi}{}_a D_x D^{vi}{}_y M_{2-a}$$

where the subscript x is a number greater than 500 preferably greater than 600, more preferably greater than 700, and most preferably greater than 800, the subscript y is a number ranging from zero to about 20, preferably ranging from zero to about 10, more preferably ranging from zero to about 5, and most preferably ranging from zero to about 4, the subscript a is a number ranging from 0 to 2, subject to the limitation that a +y is within the range of from 1 to about 20, preferably from one to about 10, more preferably from about 1.5 to about 10, and most preferably from about 1.5 to about 6, with $M^{vi}$ defined as:

$$R^1R^2R^3SiO_{1/2}$$

where $R^1$ is a monovalent unsaturated hydrocarbon radical having from two to ten carbon atoms, preferably styryl, allyl and vinyl, more preferably allyl and vinyl and most preferably vinyl and $R^2$ and $R^3$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl with D defined as:

$$R^4R^5SiO_{2/2}$$

where $R^4$ and $R^5$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl; with $D^{vi}$ defined as: $D^{vi} = R^6R^7SiO_{2/2}$ where $R^6$ is a monovalent unsaturated hydrocarbon radical having from two to ten carbon atoms, preferably styryl, allyl and vinyl, more preferably allyl and vinyl and most preferably vinyl and $R^7$ is independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl and with M defined as $M = R^8R^9R^{10}SiO_{1/2}$ with $R^8$, $R^9$, and $R^{10}$ each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl and (2) a resin having the formula:

$$(M^H{}_w Q_z)_j$$

where Q has the formula $SiO_{4/2}$ and where $M^H$ has the formula $H_b R^{11}{}_{3-b}SiO_{1/2}$ with the subscript b ranging from 1 to 3, where $R^{11}$ is a one to forty carbon atom monovalent hydrocarbon radical, preferably a one to twenty carbon monovalent hydrocarbon radical, more preferably selected from the group consisting of methyl, ethyl, propyl, iso-propyl, n-butyl, iso-butyl, sec-butyl, tert-buty, pentyl, hexyl, heptyl, phenyl, benzyl, and mesityl; and most preferably selected from the group consisting of methyl and phenyl with the subscripts w and z having a ratio of 0.5 to 4.0 respectively, preferably 0.6 to 3.5, more preferably 0.75 to 3.0, and most preferably 1.0 to 3.0; and the subscript j ranging from about 2.0 to about 100, preferably from about 2.0 to about 30, more preferably from about 2.0 to about 10, and most preferably from about 3.0 to about 5.0; and (3) a silicone, wherein the mixture of (3) with the reaction product of (1) and (2) has been subjected to shearing forces that affect the average particle distribution and the distribution has certain unique properties.

The hydrosilylation reaction is carried out in the presence of a hydrosilylation catalyst selected from the group of ruthenium, osmium, rhodium, iridium, palladium and platinum hydrosilylation catalysts. Exemplary of such catalysts are those described in U.S. Pat. Nos. 2,823,218; 3,159,601; 3,159,662; and 3,775,452.

Applicants define the silicone, component (3), as any organo-silicon compound having a viscosity below about 1,000 centistokes at 25° C., preferably below about 500 centistokes at ° C., more preferably below about 250 centistokes at 25° C., and most preferably below 100 centistokes at 25° C. Thus low molecular weight cyclic silicones such as $D_3$, $D_4$, $D_5$, and $D_6$ (i.e. $D_f$ where the subscript f ranges from 3 to 6) where D is as previously defined with $R^4$ and $R^5$ preferably methyl as well as low molecular weight linear silicones having the formula $$M'D'_iM'^{40}$$

where the substituents on D' are independently selected from the same substituents as previously defined for D and M' has the formula $$R^{12}R^{13}R^{14}SiO_{1/2}$$

where $R^{12}$, $R^{13}$ and $R^{14}$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl; and the subscript i ranges from 0 to about 300, preferably from 0 to about 100, more preferably from 0 to about 50, and most preferably from 0 to about 20 are such volatile, silicones. Preferably component (3) is a volatile low molecular weight silicone.

The materials used to prepare the gels of the present invention have been defined in terms of formulas that recite structural elements M, D, T and Q within the definitions commonly accepted in the practice of silicone chemistry. As individual molecules, or as pure compounds, the subscripts of these formulas can assume only integral values (including zero where appropriate). As complex mixtures of compounds, each of which individually satisfies the molecular definition, the subscripts in describing the mixture will assume non-integral values (including zero where appropriate). However, those non-integral values for a given subscript will still range between the upper limit and the lower limits of the range for that particular subscript when integral values are stipulated. Thus, for example in the pure compound description of component (1), the subscript a may have the values 0, 1 or 2. As a mixture of compounds, component (1) will have an average value for the subscript a that is dependent on the number of individual molecular species having a value for the subscript a that is equal to 0, 1, and 2. The same explanation holds for components (2) and (3).

Thus, the average subscripts for component (1), when component (1) is a vinyl functionalized silicone as the specific alkenyl functionalization and is a mixture of various vinyl containing compounds, as defined, will span a range of vinyl equivalent weights ranging from about 1,500 to about 150,000, preferably from about 4,500 to about 110,000, more preferably from about 10,000 to about 70,000, and most preferably from about 15,000 to about 45,000. It is to be noted that these equivalent weights are specific equivalent weights for vinyl substitution, substitution with other olefinic substituents would generate a different but comparable range of equivalent weights. Likewise, the average subscripts for component (2) as a mixture, as defined, will span a range of hydride equivalent weights ranging from about 80 to about 190, preferably from about 82 to about 170, more preferably from about 85 to about 150, and most preferably from about 87 to about 130.

Further it is desirable that the alkenyl functionality present in component (1) ranges on average of from about 1 to about 20 alkenyl groups per molecule, preferably from about 1 to about 10 alkenyl groups per molecule, more preferably from about 1.5 to about 10 alkenyl groups per molecule, and most preferably from about 1.5 to about 6 alkenyl groups per molecule. Additionally, it is desirable that the hydride functionality present in component (2) ranges on average of from about 8 to 400 SiH groups per molecule, preferably from about 8 to about 100 SiH groups per molecule, more preferably from about 8 to about 50 SiH groups per molecule, and most preferably from about 8 to about 20 SiH groups per molecule.

Components (1) and (2) (as pure compounds or mixtures) are catalytically reacted together in the presence of component (3) to produce a gel having a polymer content that is approximately from about 5 to about 75 weight percent crosslinked polymer, preferably from about 10 to about 60 weight percent crosslinked polymer, more preferably about 15 to about 40 weight percent crosslinked polymer, and most preferably about 20 to about 35 weight percent crosslinked polymer with the balance being the volatile, low molecular weight silicone oil. Once this initially produced gel is prepared, it is mixed with an additional quantity of a volatile, low molecular weight silicone, i.e. additional component (3) which is possibly different from the component (3) used to prepare the initially produced gel, and subjected to mixing or shearing forces to produce a uniform liquid gel that is from about 1 to about 25 weight percent crosslinked polymer, preferably from about 2 to about 20 weight percent crosslinked polymer, more preferably from about 3 to about 15 weight percent crosslinked polymer, and most preferably from about 3 to about 10 weight percent crosslinked polymer with the balance being the volatile, low molecular weight silicone oils, component (3) or a mixture of compounds satisfying the definition of component (3).

The gel initially produced is sufficiently viscous that liquid flow is not ordinarily observable. As a crosslinked polymeric material, the gel initially produced, having 25 weight percent crosslinked polymer network, has a Durometer hardness number, ASTM D-2240-91, of at least 5, preferably of at least 7, more preferably of at least 10 and most preferably of at least 15. ASTM test numbers for the Durometer hardness test are indicative of a material sufficiently resistant to flow that it may fairly be characterized as a solid.

In recent years, the personal care industry has found that the use of a variety of silicone polymers ranging from very low to very high molecular weight can provide improved product flow and a smooth, non-greasy feel in a wide range of applications. So for example, silicone polymers have been used in formulations for antiperspirant/deodorants, skin lotions, creams, hair care, cosmetics and the like. While these silicone polymers provide the desired performance characteristics to personal care products, they have traditionally required a delivery system that includes non-silicone thickening agents. These non-silicone thickening agents are generally undesirable as they have a negative impact on the desired silicone feel.

Recent technology that teaches the use of crosslinked silicone polymers for thickening agents fails to recognize the need to generate the unique and desirable distribution of crosslinked silicone polymer particles that create superior performance characteristics including the smooth silky feel and high viscosity for optimal thickening effects. This technology does not adequately define a process for generating the most highly desired distribution of these particles.

In addition, some of the processing methods suggested by this technology are limited to only a small range of crosslinked silicone polymer that can be useful in the instant invention. Thus as the nature of the crosslinked silicone polymer changes to provide for the desirable, more efficient use of polymer material, the suggested shearing methods using low levels of compression (colloid mills and the like), mechanical cutting shear (rotor/stator mills) or fracture (hammer mills) fail to provide the desired crosslinked silicone polymer particles of the required size and distribution. Further, they fail to define a method for processing the crosslinked silicone polymer in an economical manner.

Surprisingly a process has been discovered for providing a thickener for carrier silicone oil comprising the use of silicone particles having a unique distribution of particle sizes. Further, it has been discovered that the use of high flow induced shear and particle elongation in addition to providing an economical method for processing crosslinked silicone polymers, also generates a unique and highly desirable particle size distribution that provides the desired smooth, silky feel while maintaining high viscosity and thickening properties. Further this method of processing is applicable to the entire range of desirable crosslinked silicone polymers.

While some of the physical properties of the thickening agent are determined by the chemical structure of the crosslinked silicone polymer, the particle size and distribution are key to the highly desirable thickening (viscosity) and feel properties of the product. The efficient thickening behavior is the result of having large particle sizes present to increase the fluid viscosity. The size of the large particles is limited by the need to avoid particle so large that they form visible balls of gel during application. The superior feel is the result of generating smaller particles that improve lubricity during spreading on the skin. If the crosslinked silicone polymer is degraded to too small particles or to homogeneous fluids, they become undesirably heavy or greasy in feel. Thus preparing an efficient thickening agent with the superior feel requires the ability to generate a wide distribution of particles.

Surprisingly, the use of flow induced shear and particle elongation particularly at high stress levels provides a unique distribution of particle sizes when used to process crosslinked silicone polymers. Where as the normal expectation is to find a monomodal or possibly bimodal distribution of particle sizes when employing stress to break down particles, it is found that particularly high flow induced shear and particle elongation produce multiple distributions of particle sizes.

Earlier experiments have shown that the particles prepared in this invention are not fully swollen in material as dilute as five percent elastomer content and 95% cyclic siloxanes. However, if the elastomer is further diluted below elastomer contents of about three percent, the particle swells to its full extent. Thus the particle sizes reported in this invention demonstrate fully extended particles, while those used in most applications are of proportionally smaller actual volume depending on the available solvent. Since for a given particle composition it is possible to measure how much additional solvent may be absorbed, it is possible to back calculate the particle size for any given concentration once the full extended particle size is known. Further, it is within the scope of this invention to prepare smaller particles at a higher elastomer concentration and then swell them at a later time with additional solvent to achieve a larger particle size.

For the product of this invention, the particle size distribution comprises a multiple series of individual and often overlapping particle size populations. Taken together they provide a broad distribution of both large and small particles that impart both high efficiency and viscosity as well as a good feel and lubricity. The individual particle size populations generally fit a log normal particle size distribution and as measured at full range from an average of about 10 microns to an average of about 600 microns. When for a specific application the particles are not fully swollen, the population of particle sizes, i.e. the particle size distribution, will cover proportionally smaller sizes and with a shift to ranges over lower particle sizes. The particle size distribution comprises a series of multiple, identifiable particle populations ranging from less than about 1 microns on swelling to about 600 microns after swelling. It is preferable for the average particle size range when measured in a fully swollen state to cover from about 1 to about 500 microns, more preferably to include about 1 to about 400 microns and most preferably to include about 1 to about 300 microns after solvent swelling.

The compositions of the present invention are characterized by being dispersions of an organic polymeric elastomer, preferably a silicone elastomer, in a suitable solvent and having a particle size distribution characterized by the presence of three local maxima in the particle size distribution: 1) a local maximum ranging from about 21 to about 26 microns, 2) a local maximum ranging from about 33 to about 38 microns, and 3) a local maximum ranging from about 50 to 60 microns. As local maxima, these three local maxima appear as identifiable spikes in a plot of population versus particle diameter. It is to be emphasized that the compositions of the present invention may possess more than these three local maxima in a plot of population versus particle size, but the compositions of the present invention always possess these three local maxima. Depending on other features of the particle size distribution, the subjective properties of the composition vary from a so-called stiff creamy feel when the distribution is skewed to higher particle diameters to a light creamy feel when the distribution is centered around these three local maxima to a heavy greasy feel when the distribution is skewed to lower particle diameters. These numbers are specific to the instrumental method of analyzing the particle size distribution, specifically using a Malvern Mastersizer fitted with a 300 mm lens.

The process for making suitable crosslinked silicone polymer particles for use in the current application involves the preparation of a crosslinked silicone polymer, often in a low molecular weight silicone fluid. The material may then be further swollen with additional solvent either the same or different than that used in making the crosslinked silicone polymer. The crosslinked silicone polymer is then subjected to force to break it into small particles often in the presence of additional silicone fluid. It is the discovery of this invention that the superior method of breaking the polymer into small particles is through high flow induced shear. In this method, the slurry is first diluted, including the crosslinked silicone polymer and any additionally desired solvent, and then forced through an orifice under pressure generating flow induced shear and particle elongation. In this method, the flow induced shear and particle elongation occur both as the material passes through the orifice and in the entry region to the orifice. Although some material may be cleaved by hitting the edge of the orifice, it is this flow induced shear and particle elongation that ultimately tears the crosslinked silicone polymer apart and creates small particles.

The magnitude and profile of the flow induced shear in this process is controlled by several parameters including the pressure, orifice geometry and fluid viscosity which in part reflects the temperature, flow and shear characteristics of the fluid. Pressure may be defined as the pressure drop across the orifice. Increasing pressure drop increases the flow induced shear such that the crosslinked silicone polymer is more rapidly torn into the desired particle sizes and with a wider, more desirable distribution of particle sizes. Generally, high flow induced shear is associated with higher pressure drops for a particular orifice geometry and fluid viscosity.

The orifice geometry at a given pressure drop also determines the nature of high flow induced shear. Orifice geometry is a very flexible characteristic with a variety of shapes and sizes. Thus for example, an orifice might have an opening shape that is round, ovoid, rectangular or annular. Such orifices may be completely open or contain a pin or other obstruction at the opening. There may be one opening or many of the same or different geometries. In general as the orifice gets larger at the same pressure and fluid viscosity, the distribution of particle sizes becomes wider and more desirable. Similarly the length of the path traveled by the fluid may be long or short, straight or bent. In general as the length of the orifice becomes shorter, the flow induced shear increases and smaller more widely distributed particles are generated. The orifice size also influences flow induce shear in the entry region to the orifice. Thus as the ratio increases such that the material flows from a larger tube to a smaller orifice the particle size distribution is increased.

Fluid viscosity also determines the flow induced shear. As the viscosity of the fluid increases, the flow induced shear increases with the attendant desirable results. Viscosity will be influenced by the temperature, a lower more constant temperature giving higher viscosity is desirable. Similarly, materials exhibiting shear thinning, as some silicones are known to do, will have a lower flow induced shear in the orifice, thus increasing the particle size and narrowing the distribution. While the viscosity of the initial slurry of elastomer fed to the process may be difficult to measure, after processing the viscosity can be measured and for the first several passes through the process the viscosity of the elastomer dispersion increases. Because the material being processed is a dispersion or suspension of elastomer particles in a solvent, viscosity may be affected by a consideration of the so-called solids level. As the solids level is increased, i.e. the amount of solvent present being progressively reduced, resistance to flow increases, which can sometimes be measured as an increase in viscosity.

Taken together, these parameters are the major factors in determining flow induced shear. Depending upon a particular environment, any one or more of these three may be the dominant, i.e. most critical factor(s), in deciding the actual flow induced shear. High dynamic shear is that which is sufficient to break down the crosslinked particles to the desired size and distribution. In some instances this is accomplished in a single pass through the orifice, or alternatively a few to several passes may be required to achieve the desired particle size. In general fewer passes and wider particle size distribution are the more desired economic and performance results coming from high flow induced shear.

Flow induced particle elongation occurs as the crosslinked silicone polymer converges under pressure as it is forced to flow toward the orifice, flowing from a large diameter environment to the small diameter opening. As the particle travels through this region, it is elongated and smaller particles generated. The critical factors include pressure, fluid viscosity and the ratio of the cross sectional areas of the feed chamber to orifice. As the pressure is increased the particle elongation is increased and more efficient particle size breakage is achieved. Similarly, as the viscosity of the fluid is increased, the particle elongation is increased. As the ratio of the cross sectional areas of the feed chamber to the orifice is increased, the particle elongation is increased. In general as the particle elongation increases the efficiency in breaking down particles increases requiring fewer passes.

The pressure range desirable for sufficient flow induced shear and particle elongation is above 500 psi. Preferably it is above 1000 psi, more preferably over 1500 psi and most preferably over 2000 psi . The viscosity should be above 500 ctks. Preferably is should be over 750 ctks more preferably over 1000 ctks and most preferably over 5000 ctks. The orifice size is limited by the ability of the pumping system to maintain sufficient pressure. As a practical matter it is desirable to have an orifice size of less than 0.5 square inches, preferably less than 0.1 square inches, more preferably less than 0.05 sq. in, and most preferably less than 0.01 sq. inch.

The interaction of all of these operating variables combine to produce a process where the elastomer dispersion is reduced in average particle size and the unique particle size distribution is produced. Generally unless the elastomer dispersion is processed at a very high pressure drop, conversion to a desirable composition is not achieved in a single pass. There is thus a correlation between the applied pressure drop and the number of passes through the processing equipment that the elastomer dispersion must be subjected to in order to convert the material to the desired composition. This is reflected by the following dimensionless correlation equation that determines the number of passes, $N_p$ necessary to produce acceptable material for a given pressure drop, $P_d$:

$$N_p = 82{,}799 P_d^{(-1.1696)}$$

To some extent this equation is arbitrary and varies as the definition of what constitutes acceptable material. Material possessing a particle size distribution characterized by three peaks or three local maxima in the particle size distribution: 1) a local maximum ranging from about 21 to about 26 microns, 2) a local maximum ranging from about 33 to about 38 microns, and 3) a local maximum ranging from about 50 to 60 microns constitutes material that is acceptable.

Further, it is possible to generate a dimensionless correlation which correlates the resulting average particle size (as determined by a Malvern Mastersizer™), $S_p$(avg.), with the pressure drop, $P_d$, orifice cross-sectional area, $O_a$, and the number of passes, $N_p$.

$$S_p(\text{avg.}) = K + C_1 P_d + C_2 O_a + C_3 N_p,$$

where K is an intercept, and the various $C_i$'s are coefficients associated with the indicated variable, i.e. $C_1$ is the pressure drop coefficient, $C_2$ is the orifice cross-sectional area coefficient, and $C_3$ is the number of passes coefficient. The various operating ranges are defined in the following tables:

TABLE A

| Parameter | Operating Ranges | |
|---|---|---|
| | Minimum (from about) | Maximum (to about) |
| $P_d$ | 500 | 35000 |
| $O_a$ | 0.5 | 0.0001 |
| $N_p$ | 1 | 100 |

TABLE A-continued

Operating Ranges

| Parameter | Minimum (from about) | Maximum (to about) |
|---|---|---|
| $S_p$ (avg.) | 585 | 16 |
| K | 639 | 639 |
| $C_1$ | −0.026 | −0.026 |
| $C_2$ | −61 | −61 |
| $C_3$ | 2.87 | 2.87 |

TABLE B

Preferred Operating Ranges

| Parameter | Minimum (from about) | Maximum (to about) |
|---|---|---|
| $P_d$ | 1000 | 30000 |
| $O_a$ | 0.1 | 0.002 |
| $N_p$ | 1 | 50 |
| $S_p$ (avg.) | 3 | 610 |
| K | 639 | 639 |
| $C_1$ | −0.026 | −0.026 |
| $C_2$ | −61 | −61 |
| $C_3$ | 2.87 | 2.87 |

TABLE C

More Preferred Operating Ranges

| Parameter | Minimum (from about) | Maximum (to about) |
|---|---|---|
| $P_d$ | 1500 | 27500 |
| $O_a$ | 0.005 | 0.0003 |
| $N_p$ | 1 | 30 |
| $S_p$ (avg.) | 10 | 603 |
| K | 639 | 639 |
| $C_1$ | −0.026 | −0.026 |
| $C_2$ | −61 | −61 |
| $C_3$ | 2.87 | 2.87 |

TABLE D

Most Preferred Operating Ranges

| Parameter | Minimum (from about) | Maximum (to about) |
|---|---|---|
| $P_d$ | 2000 | 25000 |
| $O_a$ | 0.01 | 0.0005 |
| $N_p$ | 1 | 10 |
| $S_p$ (avg.) | 18 | 589 |
| K | 639 | 639 |
| $C_1$ | −0.026 | −0.026 |
| $C_2$ | −61 | −61 |
| $C_3$ | 2.87 | 2.87 |

Because the number of passes, $N_p$, correlates with the pressure drop, $P_d$, the equation for the number of passes may be substituted into the average particle size option. This mathematical substitution underscores the strong pressure drop dependence of the process. Simply stated, the process of the present invention (to yield the composition of the present invention) is a process where an elastomer dispersion is subjected to a pressure and passed through an orifice at a specified pressure drop wherein the average particle size is reduced and the particle size distribution yields certain specified local maxima. Any process that achieves this conversion by means of a pressure drop and an orifice is a process of the present invention. Applicants note that the pressure drop as used herein has the dimensions of pounds per square inch (psi.), the orifice cross-sectional area has the dimensions of square inches (sq. in. or in.$^2$), and particle sizes or average particle size has the dimension of microns. As the orifice size decreases the pressure must be increased to maintain throughput. For this reason, a smaller orifice size is listed under the column heading "maximum" in describing the ranges, because smaller orifice size and increased pressure create the same global effect.

Finally, it should be emphasized that the intercept and coefficients in the process variable equation may change depending on the specific machine used. The data presented herein represent the results of a correlation on a few selected machines and are thus illustrative rather than constituting a definition or limitation. Thus while the process variables are fairly precisely defined, the intercept, K, and the coefficients $C_1$, $C_2$, and $C_3$ are more likely to depart from the values reported herein than would the actual process variables. Irrespective of the actual machine and process conditions employed and the actual values of the intercept and these coefficients in a process variable correlation, any process accomplishing the conversion of particle size to that defined herein is intended to be covered by the appended claims.

The generation of the desired particle size is in part determined by the swelling of the particles before application of the flow induced shear and particle elongation. As the particle swells with solvent, internal stress is developed which lowers the level of shear and particle elongation required to tear apart the particle. Thus more swelling or lower crosslinked silicone polymer concentration in the slurry being processed increases the internal stress and makes the process more efficient. It is desirable to dilute to a crosslinked polymer concentration of less than 60% by weight solids. It is preferable to swell and dilute the crosslinked silicone polymer to less than 50% by weight solids, more preferable to swell the crosslinked polymer to less than 40% by weight solids and most preferable to dilute the crosslinked polymer to less than 30% by weight solids content.

The resistance to flow of the initially produced gel is overcome by high speed mixing or shearing wherein the resulting composition or mixture is a uniform liquid and has a viscosity ranging from about 500 to about 150,000 centistokes at 25° C., more preferably the resulting viscosity of the composition or mixture is from about 1,000 to about 100,000 centistokes at 25° C., and most preferably the resulting viscosity of the composition or mixture is from about 10,000 to about 60,000 centistokes at 25° C. By shearing, Applicants mean the imposition of a force upon the composition where the mixture is treated using a two roll mill, a colloid mill, a Gaulin homogenizer, a Sonolator, Ross™ mixer, Aviston™ mixer, Microfluidizer, etc.

Subjecting these compositions to a shearing force produces a component suitable for use in personal care or cosmetic applications that has an improved spreadability and an improved substance or feel because of the presence of the composition of the present invention possessing a unique particle size distribution. The personal care applications where this property is most desirable, including but not limited to, is in deodorants, antiperspirants, skin creams, facial creams, hair care products such as shampoos, mousses, styling gels, protective creams and color cosmetics such as lipsticks, foundations, blushes, makeup, and mascara; and other cosmetic formulations where silicone components have been added. The elastomer dispersions processed by the process of the present invention are comprised of a an elastomer gel and a low molecular weight silicone. The process of the present invention used to achieve the composition of the present invention may be applied to an an elastomer dispersion or a dispersion of a gel or a gel.

All United States patents referenced herein are herewith and hereby incorporated by reference.

EXPERIMENTAL

Example 1

Preparation of Crosslinked Silicon Polymers in Volatile, low Molecular Weight Silicone Oil The crosslinked silicone polymers were prepared by mixing a given silyl hydride species, a given vinyl species, and a volatile low molecular weight silicone oil in a reaction vessel and mixing. To such a mixture a standard hydrosilylation catalyst was added. Hydrosilylation in the presence of platinum catalysts is described in U.S. Pat. Nos. 3,159,601; 3,159,662; 3,220,972; 3,715,334; 3,775,452; and 3,814,730 herewith and hereby incorporated by reference. The mixture containing the hydrosilylation catalyst was heated and allowed to react at a given. Thus, for example, 1.11 grams of $(M^H{}_2Q)_4$, w=2, z=1, and j=4,250 g of a vinyl terminated siloxane having an equivalent weight of 33,750 grams/equivalent vinyl, and 650 g of octamethylcyclotetrasiloxane were added to a dough mixer and stirred. 100 g of 0.11% platinum catalyst in octamethylcyclotetrasiloxane was added. The reaction was stirred and heated to 80° C. for two hours. The reaction was cooled and the product was isolated. Following this general procedure compositions A through T were prepared. The vinyl siloxane was varied 20 through these preparations:

1) divinyl siloxane (A) is $M^{Vi}D_xM^{Vi}$ where $R^1R^2R^3SiO_{1/2}$ where $R^1$ is $(CH_2=CH)$ and $R^2$ and $R^3$ are each independently $CH_3$, and D is $R^4R^5SiO_{2/2}$ where $R^4$ and $R^5$ are each independently $CH_3$; with x varied from approximately 450 to approximately 1250;

2) monovinyl siloxane (B) is $M^{Vi}D_yM$ where $M^{Vi}$ is $R^1R^2R^3SiO_{1/2}$ where $R^1$ is $(CH_2=CH)$ and $R^2$ and $R^3$ are each independently $CH_3$, D is $R^4R^5SiO_{2/2}$ where $R^4$ and $R^5$ are each independently $CH_3$, with y approximately equal to 200 and M is $R^8R^9R^{10}SiO_{1/2}$ with $R^8$, $R^9$, and $R^{10}$ each independently $CH_3$; and 3) pentavinyl siloxane (C) is $MD_iD^{Vi}{}_kM$ where M is $R^8R^9R^{10}SiO_{1/2}$ with $R^8$, $R^9$, and $R^{10}$ each independently $CH_3$, D is $R^4R^5SiO_{2/2}$ where $R^4$ and $R^5$ are each independently $CH_3$, with i approximately equal to 200, and $D^{vi}$ defined as: $D^{vi}=R^6R^7SiO_{2/2}$ where $R^6$ is $(CH_2=CH)$ and $R^7$ is independently $CH_3$, with k approximately equal to 5.

TABLE 1

Preparation of Crosslinked Polymeric Siloxane in Volatile, Low Molecular Weight Silicone Oil: $(M^H{}_2Q)_4$ Resin Reacted with Divinyl Terminated Siloxane (A)

| Comp'n | Si—H to Si-Vinyl Ratio | Divinyl Siloxane A, mol. wt. | Polymer, wt. % | Volatile, Low Mol. Wt. Silicon, wt. % | Platinum, ppm |
|---|---|---|---|---|---|
| A | 0.7/1.0 | 66800 | 25 | 75 | 10 |
| B | 0.9/1.0 | 66800 | 25 | 75 | 10 |
| C | 1.0/1.0 | 66800 | 25 | 75 | 10 |
| D | 1.1/1.0 | 66800 | 25 | 75 | 10 |
| E | 1.3/1.0 | 66800 | 25 | 75 | 10 |
| F | 1.5/1.0 | 66800 | 25 | 75 | 10 |
| G | 1.58/1.0 | 66800 | 25 | 75 | 10 |
| H | 1.3/1.0 | 33500 | 25 | 75 | 10 |
| I | 1.3/1.0 | 92700 | 25 | 75 | 10 |
| J | 1.3/1.0 | 66800 | 25 | 75* | 10 |
| U | 1.3/1.0 | 66800 | 50 | 50 | 5 |
| V | 1.3/1.0 | 66800 | 15 | 85 | 5 |

Note:
*With the exception of preparation J which utilized D5 (decamethylcyclopentasiloxane) all the other preparations utilized D4 (octamethylcyclotetrasiloxane).

Preparations A through G study variations in the hydride to vinyl ratio of the hydrosilylation reaction. Preparations E, H and I study variations in the molecular weight of the vinyl component of the hydrosilylation reaction. Preparations E and J study variations in the volatile, low molecular weight silicone oil.

The following preparations utilized a mixture of vinyl siloxane compounds, divinyl siloxane A and monovinyl siloxane B, in contrast to those preparations presented in Table 1 which utilized only one vinyl siloxane compound, divinyl siloxane A.

TABLE 2

Preparation of Crosslinked Polymeric Siloxane inn Volatile, Low Molecular Weight Silicone Oil: $(M^H{}_2Q)_4$ Resin Reacted with Mixed Divinyl Terminated Siloxane (A) and Monovinyl Siloxane (B)

| Comp'n | Si—H to Si-Vinyl Ratio | Divinyl Siloxane A, mol. wt. | Monovinyl Siloxane B, mol. wt. | A/B | Polymer, wt. % | Volatile, Low Mol. Wt. Silicone, wt. % | Platinum, ppm |
|---|---|---|---|---|---|---|---|
| K | 1.3/1.0 | 66800 | 15900 | 90/10 | 25 | 75 | 10 |
| L | 1.3/1.0 | 66800 | 15900 | 80/20 | 25 | 75 | 10 |
| M | 1.3/1.0 | 66800 | 15900 | 70/30 | 25 | 75 | 10 |

TABLE 2-continued

Preparation of Crosslinked Polymeric Siloxane inn Volatile, Low Molecular Weight Silicone Oil: $(M^H{}_2Q)_4$ Resin Reacted with Mixed Divinyl Terminated Siloxane (A) and Monovinyl Siloxane (B)

| Comp'n | Si—H to Si-Vinyl Ratio | Divinyl Siloxane A, mol. wt. | Monovinyl Siloxane B, mol. wt. | A/B | Polymer, wt. % | Volatile, Low Mol. Wt. Silicone, wt. % | Platinum, ppm |
|---|---|---|---|---|---|---|---|
| N | 1.3/1.0 | 66800 | 15900 | 60/40 | 25 | 75 | 10 |
| o | 1.3/1.0 | 66800 | 15900 | 50/50 | 25 | 75 | 10 |
| P | 1.1/1.0 | 66800 | 15900 | 90/10 | 25 | 75 | 10 |
| Q | 1.1/1.0 | 66800 | 15900 | 70/30 | 25 | 75 | 10 |
| R | 1.1/1.0 | 66800 | 15900 | 50/50 | 25 | 75 | 10 |

Preparations K through O vary the ratio of divinyl siloxane A to mon-vinyl siloxane B at a constant hydride to vinyl ratio. Preparations P through R again vary the ratio of divinyl siloxane A to mon-vinyl siloxane B but at a different constant hydride to vinyl ratio from that in K through O.

The following preparations utilized a mixture of vinyl siloxane compounds, divinyl siloxane A and pentavinyl siloxane C, in contrast to those preparations presented in Table 1 which utilized only one vinyl siloxane compound, divinyl siloxane A.

TABLE 3

Preparation of Crosslinked Polymeric Siloxane inn Volatile, Low Molecular Weight Silicone Oil: $(M^H{}_2Q)_4$ Resin Reacted with Mixed Divinyl Terminated Siloxane (A) and Pentavinyl Siloxane (C)

| Comp'n | Si—H to Si-Vinyl Ratio | Divinyl Siloxane A, mol. wt. | Pentavinyl Siloxane B, mol. wt. | A/B | Polymer, wt. % | Volatile, Low Mol. Wt. Silicone, wt. % | Platinum, ppm |
|---|---|---|---|---|---|---|---|
| S | 1.3/1.0 | 66800 | 16200 | 90/10 | 25 | 75 | 10 |
| T | 1.3/1.0 | 66800 | 16200 | 80/20 | 25 | 75 | 10 |

The preparations reported in Table 3 vary the mixture of vinyl siloxanes being used to prepare the crosslinked material from that reported in Table 2.

Example 2

Dilution of Crosslinked Gels with Volatile, Low Molecular Weight Silicone Oils

The crosslinked gels prepared in example 1 were further diluted with volatile, low molecular weight silicone oils to produce a slurry. The volatile, low molecular weight silicone oils used for dilution were either the same as that used to prepare the crosslinked gel or different. The slurry was subjected to shearing forces in a homogenizer to produce a clear product of a desired viscosity for a specific cosmetic application. The viscosity of the gel volatile slurry that had been subjected to shearing forces ranged from about 100 centistokes to over about 100,000 centistokes at 25° C. Thus for example, 400 g of preparation E was blended with 1,600 g of $D_4$, octamethylcyclotetrasiloxane. Preparation E contains 25 wt. % crosslinked polymer, i.e. 100 g, and therefore the slurry of E in $D_4$ is 5 weight percent polymer. The mixture of 5 wt. % crosslinked polymer in $D_4$ was passed through a Gaulin homogenizer at 7,000 psi pressure. The resulting material was clear and had a viscosity of 120,000 centistokes at 25° C. The preparation of other material according to this general procedure is reported in Table 4.

TABLE 4

Viscosity of Sheared Crosslinked Silicone Polymers Diluted to 5 Wt. %

| Comp'n | Table 1 Gel | Wt. % Gel | Wt. % Volatile, Low Molecular Weight Silicone | Viscosity, cps at 25° C. |
|---|---|---|---|---|
| AA | A | 5 | 95 | 28,400 |
| BB | B | 5 | 95 | 35300 |
| CC | C | 5 | 95 | 61,800 |
| DD | D | 5 | 95 | 74,100 |
| EE | E | 5 | 95 | 115,000 |
| FF | F | 5 | 95 | 110,000 |
| GG | G | 5 | 95 | 112,000 |
| HH | H | 5 | 95 | 47,300 |
| II | I | 5 | 95 | 31,400 |
| JJ | J | 5 | 95 | 80,000 |
| KK | K | 5 | 95 | 72,700 |
| LL | L | 5 | 95 | 49,000 |
| MM | M | 5 | 95 | 27,200 |
| NN | N | 5 | 95 | 8,600 |
| OO | O | 5 | 95 | 2,500 |
| PP | P | 5 | 95 | 49,000 |
| QQ | Q | 5 | 95 | 22,000 |
| RR | R | 5 | 95 | 1,800 |

TABLE 4-continued

Viscosity of Sheared Crosslinked Silicone Polymers Diluted to 5 Wt. %

| Comp'n | Table 1 Gel | Wt. % Gel | Wt. % Volatile, Low Molecular Weight Silicone | Viscosity, cps at 25° C. |
|---|---|---|---|---|
| SS | S | 5 | 95 | 81,700 |
| TT | T | 5 | 95 | 93,100 |
| UU | U | 6 | 94 | 20,000 |
| VV | V | 3.5 | 96.5 | 122,000 |

These data indicate that:
1) as hydride to alkenyl (vinyl) ratio is changed through 0.7 to 1.6 (hydride) to 1.0 (alkenyl) the product gel viscosity increases;
2) as the molecular weight of the alkenyl component increases, extending the distance between crosslink sites,
  i) the ability of the initially produced polymer gel to swell upon the addition of volatile silicones increases and
  ii) the viscosity increases; and
3) increasing the average functionality of the alkenyl precursor from 1.3 to 2.0, increases the crosslink density and the viscosity of the resulting product.

Example 3

Comparison of Low Crosslink Density Gels with High Crosslink Density Gels

The processed gels of the present invention are gels that have a high crosslink density, due to the use of the $M^HQ$ resin and vinyl siloxanes that a fairly low equivalent weight with respect to the vinyl group. For purposes of comparison, gels possessing a low density crosslinking network were prepared. Thus, the procedures outline to prepare the gels of example one were utilized with a linear hydride siloxane containing only two equivalents of hydride per molecule and a vinyl siloxane containing only two equivalents of vinyl per molecule (on average). Thus 2.02 g of a hydrogen terminated siloxane having a molecular weight of about 1,818 and 75 g of a vinyl terminated siloxane having a molecular weight of 67,500 were mixed with 425 g of octamethylcyclotetrasiloxane. The mixture was stirred and 10 ppm platinum catalyst was added as previously described. The mixture was heated to 80° C. for five hours. The product was cooled and isolated. The viscosity was 88.5 centistokes at 25°C. The results demonstrate that siloxane polymers made from low functionality ingredients produce siloxane polymers with little crosslinking and thus low efficiency in controlling the viscosity of the volatile siloxanes.

Elastomer Solids Content

The percent solid elastomer in the product was determined by placing a weighed sample in an oven at 150° C. for 45 minutes and observing the weight loss.

Viscosity

The elastomer/volatile siloxane solutions after processing under flow induced shear and elongation where evaluated for viscosity 24 hours after the processing sample was taken on a Brookfield RVT Viscometer with a T-C spindle at 4 RPM.

Aesthetic Evaluation

Elastomer/volatile siloxane samples were evaluated for the presence of "gel balls" by applying a small sample to the skin and rubbing until the solvent spread and evaporated. During this process the presence of very small, undesirable balls of silicone were observed in incompletely processed material.

Particle Size

The particle size analysis was done using a Malvern Mastersizer™ fitted with a 300 mm lens. Applicants note that the particle sizes determined will vary as a function of the different type of apparatus used to determine the particle size. Thus, while a particle size appears intrinsically to be absolutely determinable, it is in fact governed by the machine used to measure it. Accordingly, the particle sizes herein recited are those determined by a Malvern Mastersizer and should other machines by used by other practitioners, those machines must be referenced or calibrated against the sizes as determined by a Malvern Mastersizer. The desired material (10 grams) generally containing 5 to 10% elastomer swollen with 90–95% cyclic siloxanes was dissolved in a 50/50 mixture (40 grams) of isopropanol (IPA) and decamethylcyclopentasiloxane (D5). This solution was then added to approximately 500 grams of a 50/50 IPA/D5 that had already been placed in the reservoir of the Malvern Mastersizer. The resulting solution was circulated through the instrument for five minutes and then triplicate measurements were taken. The limits on the Malvern Mastersizer extend from 1 to 600 microns with the 300 mm lens. A 45 mm lens was also employed to look for smaller particles with no significant number being found. Particles greater than 600 microns such as those that might cause gel balls were not visible by this method.

Earlier experiments have shown that the particles prepared in this invention are not fully swollen in material as dilute as five percent elastomer content and 95% cyclic siloxanes. However, if the elastomer is further diluted below elastomer contents of about three percent, the particle swells to its full extent. Thus the particle sizes measured in this experiment demonstrate fully extended particles, while those used in most applications are of proportionally smaller actual volume depending on the available solvent. Since for a given particle composition it is possible to measure how much additional solvent may be absorbed, it is possible to back calculate the particle size for any given concentration once the full extended particle size is known. Further, it is within the scope of this invention to prepare smaller particles at a higher elastomer concentration and then swell them at a later time with additional solvent to achieve a larger particle size.

Example 4

Preparation of Elastomer Samples

The elastomer samples were prepared by mixing the low molecular weight, volatile siloxane, vinylsiloxane and silylhydride together and mixing. This was followed by platinum catalyst addition and slow heating to 80° C. to allow cure of the elastomer. This was done with stirring to promote breaking of the resulting elastomer into pieces to accommodate the ensuing processing steps.

Thus in a typical example 7.28 gm. of $[(HMe_2SiO)_2SiO]_4$ with 0.92% hydride content, 1500 gm. of vinyl terminate polysiloxane containing 0.089% vinyl and 4500 gm. of decamethylcyclopentasiloxane were added to a 10 l Drais mixer and allowed to mix at 20° C. Platinum catalyst was then added and the temperature slowly brought to 80° C. and held for two hours. The product was then removed from the Drais and used in the following examples.

Example 5

Dilution

The 25% elastomer/volatile siloxane produced above was further diluted with the same or a different low molecular weight siloxane before being subjected to high, flow induced shear and elongation. Generally the 25% elastomer/volatile siloxane was diluted to about 5 to 7% solid elastomer content in order to facilitate processing and introduce additional stress to the crosslinked polysiloxane particle.

In a typical example 450 gm. of 25% elastomer/volatile siloxane was added to 1550 gm. of decamethylcyclopentasiloxane and allowed to swell before processing. After processing the solution was checked for solid elastomer content by the method described above and found to be 5.62%.

Example 6

Sonolator Processed Material

The diluted solution of elastomer/volatile siloxane was fed to the Sonolator unit by a pump such that a constant pressure was maintained on the orifice. Orifice size was varied through the experiments. Through-put was then measured to determine flow. Processing was done either in discreet passes or by recycling to the feed chamber with the number of passes being determined by the through-put and processing time. Samples were taken directly from the end of the sample loop at desired intervals.

Gaullen Homogenizer

The Gaullen Homogenizer was run in a manner similar to the Sonolator with respect to feeds, discreet passes and number of passes with time for extended samples. The pressure measurement was taken from the pressure measured in the feed chamber controlled by the pressure setting on the orifice pin.

Microfluidizer

The microfluidizer was generally fed material previously diluted and reduced in particle size from well over 1 mm to an average of about 1000 microns with a rotor/stator mixer. Material was then pumped through the Microfluidizer in discreet passes. The Microfluidizer was run using two chambers. In all cases the first was a H30Z chamber and the second either a J30Y or a smaller J20Y chamber.

Pressure Related Experiments

A.) The 25% elastomer/volatile siloxane product made above was diluted to approximately 5.5 % solid elastomer content with pentamethylcyclopentasiloxane. The material was cycled through a Sonolator at 300 psi and sampled as follows:

| Passes | 11.25 | 33.75 | 56 | 112 |
|---|---|---|---|---|
| Viscosity | 23150 | 23450 | 22450 | 20100 |
| Aesthetics | Gel Balls | Gel Balls | Gel Balls | Gel Balls |

The experiment shows that at low pressure over a very extended number of cycles the material did not break into sufficiently small particles to form an aesthetically acceptable material of high viscosity.

B.) Similarly, 25% elastomer/volatile siloxane was diluted to 5.62% using decamethylcyclopentasiloxane. The material was processed through the Sonolator at 1000 psi and samples taken as follows:

| Passes | 18 | 30 |
|---|---|---|
| Viscosity | 40000 | 33000 |
| Aesthetics | Slight Gel Balls | No Gel Balls |
| Particle Size Peak Center and Volume Area Percent | | |
| 23.5 micron | 0.50% | 2.54% |
| 36.5 | 8.04 | 19.23 |
| 53.0 | 24.23 | 31.93 |
| 65.1 | | 46.30 |
| 71.7 | 66.52 | |

C.) A 25% elastomer/volatile siloxane made in the manner stated above was diluted to 5.5% with decamethylcyclopentasiloxane. The material was processed through a Sonolator at 4500 psi and samples taken as follows:

| Passes | 3 | 4 |
|---|---|---|
| Viscosity | | |
| Aesthetics | No Gel Balls | No Gel Balls |
| Particle Size Peak Center and Volume Percent | | |
| 13.4 microns | 0.08% | 0.28% |
| 23.3 | 3.70 | 9.11 |
| 36.2 | 9.37 | 9.14 |
| 52.0 | 12.46 | 18.31 |
| 71.5 | 74.40 | |
| 75.0 | | 63.16 |

Experiments 6 A, B and C show that increasing the flow induced shear and elongation by increasing pressure provides a significantly faster and more economic (fewer passes to achieve acceptable aesthetics) method for processing the crosslinked polysiloxane. At the same time the product viscosity is dramatically higher in high flow induced shear and elongation samples which is a distinct advantage in requiring lower amounts of crosslinked polysiloxane in formulated products where maintaining a high viscosity cream is important. The particle size comparison of examples 6 B and C shows that the material made with 3 passes at high flow induced shear and elongation has a broader distribution of particle sizes (more large particles and more small particles) than a comparable sample made at lower flow induced shear and elongation. The result of this is that the high flow induced shear and elongation sample has an advantage in containing both higher viscosity from large particle sizes and smoother feel during application to the skin from the small particle sizes.

Example 7

A.) A 25% elastomer/volatile siloxane sample prepared as described above was diluted to 5% with an 85/15 blend of octamethylcyclotetrasiloxane and decamethylcyclopentasiloxane. The material was processed in the Gaullin Homogenizer as described above at 4000 psi and sampled as follows:

| Passes | 11 | 45 |
|---|---|---|
| Viscosity | 2640 | 20300 |
| Aesthetics | Gel Balls | Few Gel Balls |
| Particle Size | | |
| Peak Center and Volume Percent | | |
| 23.3 | | 4.32 |
| 36.2 | | 11.88 |
| 54.3 | | 28.56 |
| 88.3 | | 55.23 |

B.) A 25% elastomer/volatile siloxane sample prepared as described above was diluted to 5% with an 85/15 blend of octamethylcyclotetrasiloxane and decamethylcyclopentasiloxane. The material was processed in the Gaullin Homogenizer as described above at 7000 psi and sampled as follows:

| Passes | 5 |
|---|---|
| Viscosity | 78100 |
| Aesthetics | No Gel Balls |
| Particle Size | |
| Peak Center and Volume Percent | |
| 23.3 | 5.73 |
| 36.2 | 7.48 |
| 52.0 | 20.26 |
| 88.4 | 66.52 |

Comparison of examples 7 A and B shows that as the flow induced shear and elongation is increased by increasing the pressure, the number of passes required to make acceptable product free of gel balls is significantly reduced. In addition, with higher flow induced shear and elongation higher viscosity is obtained. Comparison of the particle size after 5 passes at high flow induced shear and elongation is broader than after 45 passes at low flow induced shear and elongation. The result is advantageous in providing higher viscosity from large particles and superior feel and flow characteristics from low particle sizes.

Example 8

A.) A 25% elastomer/volatile siloxane sample prepared as described above was diluted to 5% with an 85/15 blend of octamethylcyclotetrasiloxane and decamethylcyclopentasiloxane. The material was processed in the Microfluidizer at 6,000 psi with a sample taken as follows:

| Passes | 1 |
|---|---|
| Viscosity | <10,000 |
| Aesthetics | Gel Balls |

B.) A 25% elastomer/volatile siloxane sample prepared as described above as diluted to 5% with an 85/15 blend of octamethylcyclotetrasiloxane and decamethylcyclopentasiloxane. The material was processed in the Microfluidizer at 18,000 psi with a sample taken as follows:

| Passes | 1 |
|---|---|
| Viscosity | >60,000 |
| Aesthetics | No Gel Balls |

C.) A 25% elastomer/volatile siloxane sample prepared as described above was diluted to 5% with an 85/15 blend of octamethylcyclotetrasiloxane and decamethylcyclopentasiloxane. The material was processed in the Microfluidizer at 16,000 psi with the larger J30Y chamber and a sample taken as follows:

| Passes | 1 |
|---|---|
| Viscosity | 84400 |
| Aesthetics | No Gel Balls |
| Particle Size | |
| Peak Center and Volume Percent | |
| 24.3 | 1.49 |
| 36.1 | 3.91 |
| 51.3 | 6.98 |
| 71.2 | 34.58 |
| 117.7 | 53.03 |

Example 8 A, B and C shows that as flow induced shear and elongation is increased by increasing the pressure in a Microfluidizer, the product is more efficiently processed to aesthetically acceptable material having the desired high viscosity. The high flow induced shear and elongation also provides a broad particle size distribution.

Orifice size Related Experiments

Example 9

A.) A 25% elastomer/volatile siloxane sample prepared as described above was diluted to 5% with an 85/15 blend of octamethylcyclotetrasiloxane and decamethylcyclopentasiloxane. The material was processed in the Microfluidizer at 16,000 psi with a smaller J20Y chamber and a sample taken as follows:

| Pass | 1 |
|---|---|
| Viscosity | 172750 |
| Aesthetics | No Gel Balls |
| Particle Size | |
| Peak Center and Volume Percent | |
| 23.5 | 0.12 |
| 35.8 | 0.62 |
| 51.9 | 2.83 |
| 72.7 | 5.10 |
| 132.7 | 91.33 |

The comparison of example 9 and example 8 C shows that decreasing the orifice size while maintaining pressure diminishes the breadth of particle size distribution.

Example 10

A.) A 25% elastomer/volatile siloxane made in the manner stated above was diluted to 5.5% with decamethylcyclopentasiloxane. The material was processed through a Sonolator at 4500 psi with a 0.0021 orifice size and samples taken as follows:

| Pass | 1 |
|---|---|
| Viscosity | NA |
| Aesthetics | Gel Balls |
| Particle Size | |
| Peak Center and Volume Percent | |
| 23.4 | 0.69 |
| 35.8 | 2.16 |
| 56.7 | 15.72 |
| 111.5 | 81.43 |

B.) A 25% elastomer/volatile siloxane made in the manner stated above was diluted to 5.5% with decamethylcyclopentasiloxane. The material was processed through a Sonolator at 4500 psi with a 0.0008 orifice size and samples taken as follows:

| Pass | 1 |
|---|---|
| Viscosity | NA |
| Aesthetics | Gel Balls |
| Particle Size Peak Center and Volume Percent | |
| 23.4 | 0.39 |
| 35.8 | 1.63 |
| 60.7 | 22.21 |
| 111.5 | 75.77 |

A.) A 25% elastomer/volatile siloxane made in the manner stated above was diluted to 5.5% with decamethylcyclopentasiloxane. The material was processed through a Sonolator at 4500 psi with a 0.0021 orifice size and samples taken as follows:

| Passes | 2 |
|---|---|
| Particle Size Peak Center and Percent Volume | |
| 23.5 | 1.32 |
| 36.4 | 4.35 |
| 51.8 | 7.90 |
| 71.5 | 20.06 |
| 118.9 | 66.36 |

B.) A 25% elastomer/volatile siloxane made in the manner stated above was diluted to 5.5% with decamethylcyclopentasiloxane. The material was processed through a Sonolator at 4500 psi with a 0.0008 orifice size and samples taken as follows:

| Passes | 2 |
|---|---|
| Particle Size Peak Center and Volume Percent | |
| 23.4 | 1.39 |
| 36.4 | 4.62 |
| 52.0 | 7.84 |
| 71.4 | 21.09 |
| 120.0 | 65.05 |

Examples 10 A and B demonstrate the broader particle size distribution achieved with a wider orifice size. In these examples the crosslinked elastomer was not subjected to sufficient shear to achieve the desired aesthetic standard of no gel balls, and further passes were done. As further passes were made, examples VIII A and B, the particle size distribution for each orifice size became similar as the result of randomization of the position of the particles as they went through the orifice. In general the effects on particle size distribution of orifice size are less pronounced in the Sonolator than in the Microfluidizer reflecting the shorter orifice path length. Because of the shorter path length in the Sonolator, more of the flow induced shear and particle elongation is created as the material is compacted before entering the orifice. Since this is similar for both orifice sizes, the change with orifice size is less dramatic.

Viscosity Related Experiments

Example 12

A 25% elastomer/volatile siloxane made in the manner stated above was diluted to 5.5% with decamethylcyclopentasiloxane. 10 weight % of 350 cps viscosity polydimethylsiloxane was added and mixed in. The polydimethylsiloxane oil was observed not to completely penetrate the crosslinked polysiloxane elastomer, but rather to coat the surface causing a dramatic reduction in viscosity. This viscosity lowering was observed through the entire processing step.

The material was processed through a Sonolator with a 0.0008 orifice at 1000 psi and samples taken as follows:

| Passes | 11 | 22 | 34 | 45 | 56 |
|---|---|---|---|---|---|
| Viscosity | 400 | 400 | 400 | 400 | 400 |
| Aesthetics | Gel Balls | Gel Balls | No Gel Balls | | |
| Particle Size Peak Center and Volume Percent | | | | | |
| Passes | 11 | 22 | 34 | 45 | 56 |
| 12.8 | 0 | 0 | 0 | 0 | 0 |
| 23 | 0.05 | 0.18 | 0.40 | 0.33 | |
| 0.22 | | | | | |
| 36 | 0.58 | 1.83 | 3.52 | 4.03 | |
| 4.50 | | | | | |
| 56 | | 22.79 | 18.11 | 10.03 | |
| 7.27 | | | | | |
| 64 | 14.58 | | | | |
| 75 | | | | 85.60 | |
| 88.01 | | | | | |
| 90 | | | 77.98 | | |
| 99 | | 75.20 | | | |
| 140 | 84.79 | | | | |

Comparison of example 12 with example 6 B run at the same pressure, demonstrates that viscosity is critical in producing the particle size range. Thus when the viscosity is reduced to about 400 ctks., particles sizes remain too large through more cycles and only very slowly produce particles of small size. At low viscosity there is lower flow induced shear and elongation to break up the particles.

Particle Size Distribution Characterization Experiments

In the preparation of the material of the present invention by the process of the present invention, depending on the number of passes at a given pressure, material possessing the three particle size ranges defined as necessary for the compositions of the present invention can be prepared in proportions of those particle size ranges that differ and therefore provide subjective differences in feel.

| | Large Average Particle Size Particle Size Distribution: Material Ranging from about 100 to 600 microns | | | | | |
|---|---|---|---|---|---|---|
| Average Particle Size of Population, microns | 10–15 | 21–26 | 33–38 | 50–60 | 65–80 | 100 to 300 |
| Volume % Range | 0 | 0.1–2 | 0.1–5 | 1.0–10 | 10–50 | 40–95 |
| Peak Width at Half Height | 0 | 0.1–10 | 1–10 | 10–30 | 25–100 | 75–200 |

The material having a large average particle size from 100 to 600 microns has a thick consistency much like commercial gelatin food products. When applied to the skin, the material is hard to rub into the skin, sticks to itself rather than spreading onto the skin and does not readily wet the skin and form a thin film.

| Moderate Average Particle Size Particle Size Distribution: Material Ranging from about 50 to 150 microns | | | | | | |
|---|---|---|---|---|---|---|
| Average Particle Size of Population, microns | 10–15 | 21–26 | 33–38 | 50–60 | 65–80 | 100 to 300 |
| Volume % Range | 0.1–5 | 1–5 | 5–20 | 10–35 | 30–80 | 0–20 |
| Peak Width at Half Height | 0.1–3 | 1–15 | 5–20 | 15–40 | 40–125 | 75–200 |

The material having a moderate average particle size ranging form 50 to 150 microns has a smooth creamy pudding-like consistency. When applied to the skin, the material exhibits some resistance when rubbed on the skin producing a cushion or sponge like feel that that conveys a subjective perception of a rich fullness.

| Small Average Particle Size Particle Size Distribution: Material Ranging from about 100 to 600 microns | | | | | | |
|---|---|---|---|---|---|---|
| Average Particle Size of Population, microns | 10–15 | 21–26 | 33–38 | 50–60 | 65–80 | 100 to 300 |
| Volume % Range | 5–15 | 15–60 | 20–50 | 1–30 | 0 | 0 |
| Peak Width at Half-Height | 2–15 | 3–20 | 5–25 | 5–30 | 0 | 0 |

The material having a small average particle size has a thin fluid like consistency. When applied to the skin this material spreads readily across the skin with little or no resistance and produces an initial heavy or greasy feel. However, once applied to the skin, this material provides a smooth silky feel on the skin.

It should be noted that all three examples of a composition of the present invention possess the specific particle sizes characteristic of the invention.

Having described the invention, that which is claimed is:

1. A process comprising:
   a) subjecting a dispersion of a silicone elastomer gel in a solvent to a pressure above 500 psi, said elastomer having an initial average particple size and a particle size distribution;
   b) subjecting said dispersion to a pressure drop through an orifice, whereby said dispersion passes through said orifice, wherein the initial average particle size of said dispersion is reduced; and
   c) repeating steps a) and b), whereby said particle size distribution is controlled and comprises;
   d) a local maximum ranging from about 21 to about 26 microns;
   e) a local maximum ranging from about 33 to about 38 microns; and
   f) a local maximum ranging from about 50 to 60 microns.

2. A process comprising:
   a) subjecting a dispersion of a silicone elastomer gel in a solvent to a pressure drop using an orifice, said elastomer having an initial average particle size and a particle size distribution, whereby said dispersion passes through said orifice, wherein the initial average particle size of said dispersion is reduced; and
   b) repeating step a), whereby said particle size distribution is controlled and said particle size distribution comprises;
   c) a local maximum ranging from about 21 to about 26 microns;
   d) a local maximum ranging from about 33 to about 38 microns; and
   e) a local maximum ranging from about 50 to 60 microns.

3. A process comprising:
   a) subjecting a dispersion of a silicone elastomer in a solvent to a pressure above 500 psi, said elastomer having an initial average particle size and a particle size distribution;
   b) subjecting said dispersion to a pressure drop through an orifice, whereby said dispersion passes through said orifice, wherein the initial average particle size of said dispersion is reduced; and
   c) repeating steps a) and b), whereby said particle size distribution is controlled and comprises:
      i) a local maximum ranging from about 21 to about 26 microns;
      ii) a local maximum ranging from about 33 to about 38 microns; and
      iii) a local maximum ranging from about 50 to about 60 microns.

4. The process of claim 3 wherein said organic polymeric elastomer is a gel.

5. The process of claim 4 wherein said silicone elastomer has an ASTM D-2240-91 Durometer hardness of at least 5.

6. The process of claim 5 wherein said silicone elastomer has an ASTM D-2240-91 Durometer hardness of at least 10.

7. The process of claim 6 wherein said silicone elastomer has an ASTM D-2240-91 Durometer hardness of at least 15.

8. The process of claim 3 wherein steps a) and b) are combined.

9. The process of claim 8 wherein said multiple particle size distributions comprise:
   a) a local maximum ranging from about 21 to about 26 microns;
   b) a local maximum ranging from about 33 to about 38 microns; and
   c) a local maximum ranging from about 50 to about 60 microns.

10. The process of claim 8 wherein said silicone elastomer is gel.

11. The process of claim 10 wherein said silicone elastomer has an ASTM D-2240-91 Durometer hardness of at least 10.

12. The process of claim 11 wherein said silicone elastomer has an ASTM D-2240-91 Durometer hardness of at least 15.

* * * * *